United States Patent [19]

Yoshida et al.

[11] Patent Number: 5,011,952
[45] Date of Patent: Apr. 30, 1991

[54] PHOSPHOLIPASE A2 INHIBITOR

[75] Inventors: Tadashi Yoshida, Toyono; Keizo Inoue, Koto; Hitoshi Arita, Kawanishi; Shigeru Matsutani, Hashimoto; Jun'ichi Shoji, Hirakata; Yoshimi Kawamura, Minoo, all of Japan

[73] Assignee: Shionogi & Co., Ltd., Osaka, Japan

[21] Appl. No.: 516,982

[22] Filed: Apr. 30, 1990

[30] Foreign Application Priority Data

Apr. 28, 1989 [JP] Japan .................................. 1-109939

[51] Int. Cl.$^5$ .......................................... C07D 311/82
[52] U.S. Cl. .................................................. 549/393
[58] Field of Search ............................... 549/391, 393

[56] References Cited

PUBLICATIONS

Suarna et al., Chemical Abstracts, vol. 108, No. 17, 25 Apr. 1988, pp. 775-776, Abstract No. 150753k.
Kolly et al., Chemical Abstracts, vol. 110, No. 13, 27 Mar. 1989, p. 672, Abstract No. 114635f.
Endo et al., Chemical Abstracts, vol. 91, No. 25, 17 Dec. 1979, p. 519, Abstract No. 209363u.
Kitahara et al., Chemical Abstract, vol. 96, No. 7, 15 Feb. 1982, p. 295, Abstract No. 48698t.
Kitahara et al., Chemical Abstracts, vol. 99, No. 5, 1 Aug. 1983, p. 506, Abstract No. 38273y.
Emmono, Bulletin of the Torrey Biotanical Club, vol. 57, No. 2, Feb. 1930, pp. 123-126.

Primary Examiner—Elizabeth C. Weimar
Assistant Examiner—Pamela S. Webber
Attorney, Agent, or Firm—Wenderoth, Lind & Ponack

[57] ABSTRACT

A compound of the formula:

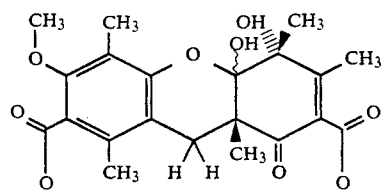
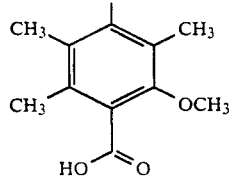
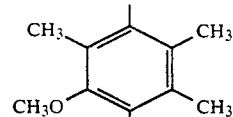
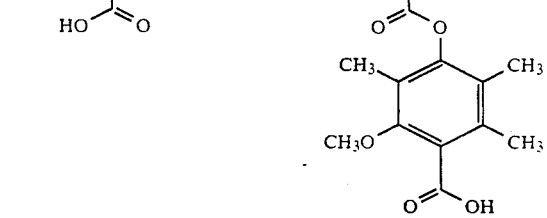

wherein the wave line means α-bond or β-bond, which compound is useful as a phospholipase A$_2$ inhibitor. Process for the production of the compound, pharmaceutical composition containing the compound, and a cell culture of a microorganism *Thielavia terricola* RF-143 producing the compound are also provided.

1 Claim, 2 Drawing Sheets

PHOSPHOLIPASE A2 INHIBITOR

The present invention relates to a novel phospholipase $A_2$ inhibitor. In particular, it relates to a physiologically active compound capable of inhibiting phospholipase $A_2$, which compound is produced by cultivating Thielavia terricola RF-143 or a variant thereof capable of producing said compound under submerged aerobic fermentation conditions.

The novel compound of the invention is represented by the formula:

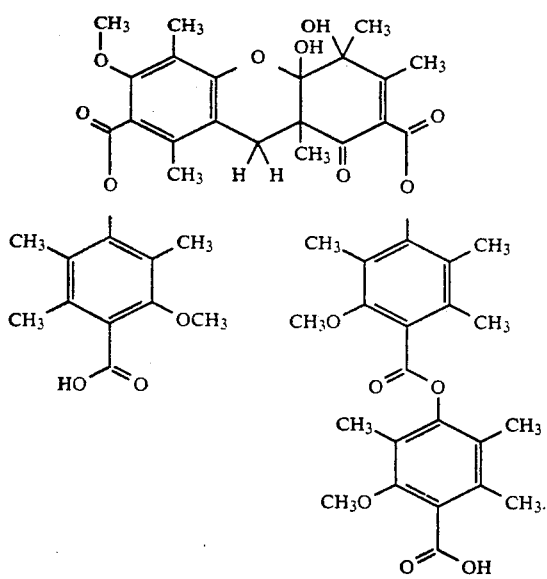

specifically, the novel compound of the invention is represented by the formula:

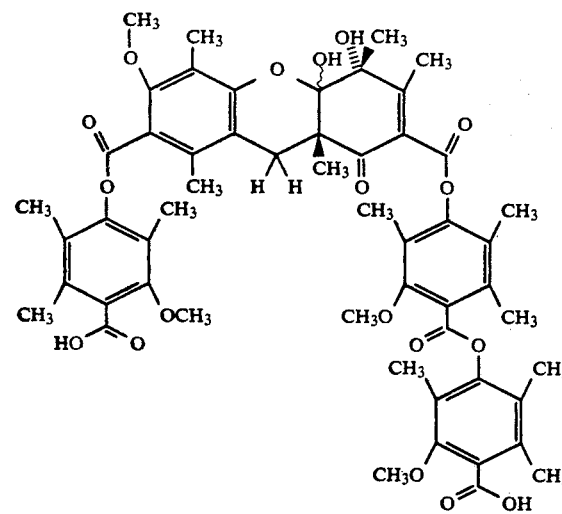

wherein the wave line means α-bond or β-bond, and the compound has been designated as "thielocin".

As will be understood from the above formula, thielocin is a mixture of α-isomer and β-isomer. Specifically, the α- and β-isomers are represented by the following formulae (A) and (B), respectively.

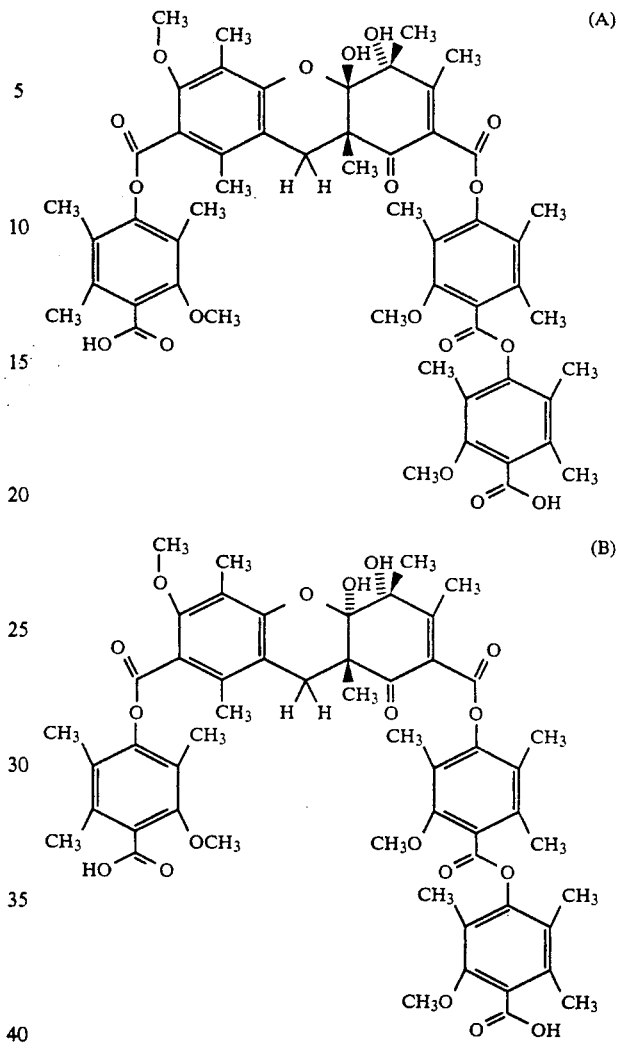

Another aspect of the present invention is to provide Thielavia terricola RF-143 and thielocin-producing variants thereof. Further aspect of the invention is a process for the production of thielocin which comprises cultivating Thielavia terricola RF-143 or a variant thereof capable of producing thielocin under submerged aerobic fermentation conditions until a substantial amount of thielocin is produced. The present invention further includes the production of α- or β-isomer which comprises separating either of them from thielocin in the form of a mixture thereof.

Phospholipase $A_2$, hereinafter referred to as $PLA_2$, which is found in secretory components or cells of various organisms, is an esterase specifically active to phosphorus-containing lipids. More particularly, $PLA_2$ specifically hydrolyzes a fatty acid ester at C-2 position of 1,2-diacylglycerophospholipid to form lysoglycerophospholipid and the fatty acid.

The enzymatic activity of $PLA_2$ often exerts toxicity to nervous system, muscles, and heart, and also causes anticoagulant, which can induce convulsion, arterial hypotension, haemolysis, hemorrhage, and edema. In addition, the esterase is possibly associated with other diseases directly or indirectly. Accordingly, it is generally recognized that a substance inhibiting the enzymatic activity of $PLA_2$ would be useful for the control or treatment of various diseases caused by, or related to, the enzymatic action of the esterase. Such inhibitory substance as mentioned above is herein referred to as $PLA_2$ inhibitor. Mepacrine and p-bromophenacyl bromide are known to be effective as the inhibitor.

The present invention provides a novel $PLA_2$ inhibitor named thielocin which is produced by cultivating *Thielavia terricola* RF-143. Thielocin produced by the cultivation is a mixture of α- and β-isomers. The isomers can be separated from each other by high pressure liquid chromatography (HPLC), although thin layer chromatography is unsuccessful. The isomers are interconvertible in a solution. The conversion rate varies depending on the nature of the solvent. When α-isomer is dissolved in a solvent, half of the molecules are apparently converted to β-isomer until a 1:1 (α-isomer:β-isomer) equilibrium is reached, and vice versa. The time necessary for reaching the equilibrium varies depending on the solvent used. Dimethylsulfoxide requires a relatively short time, i.e., about 3 hours at room temperature, while chloroform or ethyl acetate requires a longer time. When either of the isomers is dissolved in water at pH 7.0–7.5, $\alpha:\beta = 9:1-8:2$ equilibrium is rapidly obtained.

The two isomers are slightly different from each other in their physico-chemical properties, such as melting points, solubilities, IR spectra, $^1H$ NMR and $^{13}C$ NMR spectra, etc.

Although the physico-chemical properties of the isomers are somewhat different from each other as mentioned above, their physiological properties are considered almost the same. Accordingly, for the purpose of the invention, separation of them is not essential, and therefore, the term "thielocin" herein used refers to a mixture of the isomers unless otherwise stated.

The present invention further provides a biologically pure culture of *Thielavia terricola* RF-143 which produces $PLA_2$ inhibitor, thielocin. The culture of the thielocin-producing strain has been deposited, under Budapest Treaty, at the Fermentation Research Institute Agency of Industrial Science and Technology, Japan, under accession number FERM BP-2196 (Dec. 19, 1988).

Cultural characteristics of *Thielavia terricola* RF-143 are described below.

The vegetative hypha of the culture is macroscopically white in color on corn meal agar medium. The ascocarp is formed on the surface of the agar medium, which is spherical in shape and brownish black in color. The size of the ascocarp is 100–300 μm in diameter, and the texutra epidermoidea of the outer wall is brown. The ascus is $30-35 \times 15-17$ μm in size and presents a pear like shape. The ascus which dissolves when matured, contains eight ascospores. The oscospores are broadly fusiform, olive to brownish gray in color, and $12-18 \times 6-8$ μm in size, with a germ pore at one end. Imperfect stage is absent.

The above characteristics have identified the RF-143 strain as *Thielavia terricola*, which is described in the following published literatures: C. W. Emmons, Bull. Torrey Bot. Club, 57 124 (1930); G. Doguet, Rev. Mycol., 21, Suppl. Colonial 1, 2 (1956); C. Booth, Mycol. Pap. 33 37 (1961).

As is the case with other organisms, the characteristics of the thielocin-producing culture of the present invention, *Thielavia terricola* RF-143, may be subject to variation. Mutation of the strain may naturally occur, but may be easily induced by treatment with various physical and chemical mutagens. Accordingly, those skilled in the art will understand that variants of *Thielavia terricola* RF-143 fall within the scope of the invention insofar as they maintain their abilities producing a substantial amount of $PLA_2$ inhibitor.

Cultivation of *Thielavia terricola* RF-143 may be conducted by conventional methods. However, submerged aerobic fermentation in the presence of appropriate carbon sources, nitrogen sources, mineral salts, trace elements, and the like is preferred.

For production of $PLA_2$ inhibitor, thielocin, the strain is cultivated in a shake-flask at a temperature of 20°–40° C., preferably at 28° C., for ten days under aeration. Produced thielocin is then recovered from the fermentation medium by methods used in the fermentation art. For instance, the medium is filtered, and the filtrate and precipitates comprising cell mass are separately extracted with appropriate solvents. Combined extracts are concentrated, and the residue is purified by a solvent extraction, chromatography, and the like. Purified thielocin so obtained may be separated into α- and β-isomer if desired.

The amount of thielocin effective for inhibiting 50 % of $PLA_2$ activity varies depending on $PLA_2$ sources, and is 47 μg/ml for the one derived from porcine pancreas, 10 μg/ml for the one derived from snake venom, and 0.005 μg/ml for the one derived from rat platelet.

Thielocin of the invention is considered to be useful for prophylactic and therapeutic treatment of various diseases caused by enzymatic activity of $PLA_2$.

Figure 1:
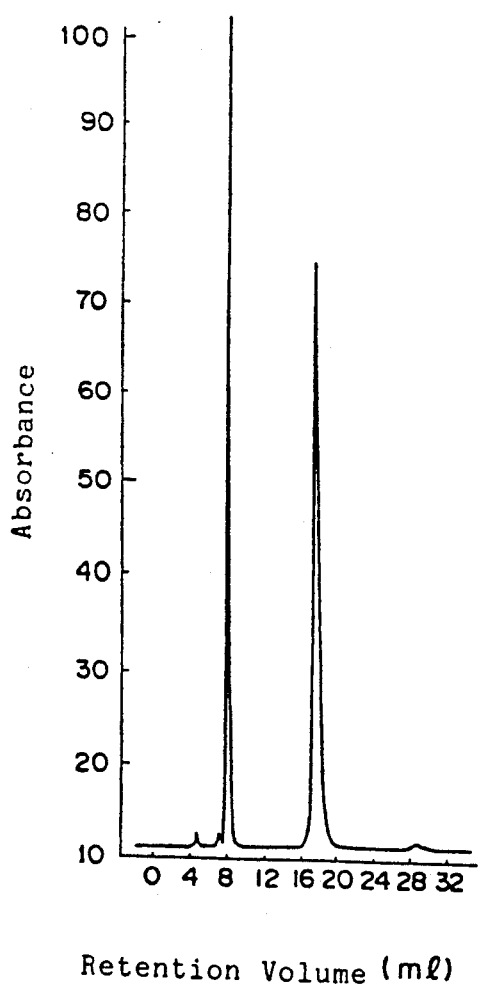
FIG. 1 shows high pressure liquid chromatogram of α-thielocin (FIG. 1 (a)) and β-thielocin (FIG. 1 (b)).
Figure 1:
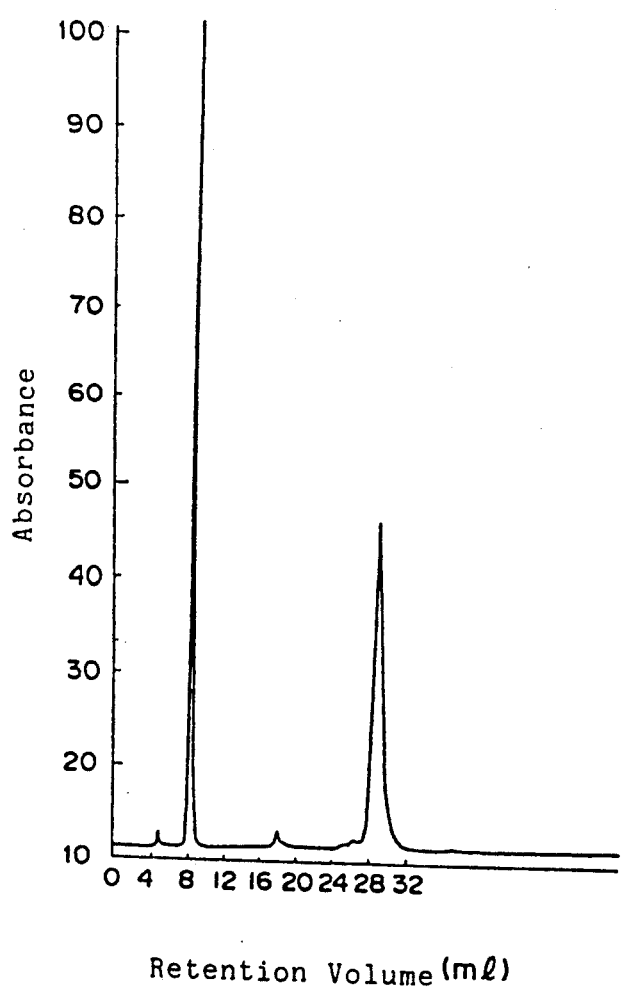

Following Examples further illustrate the present invention. The Examples are not intended to be limiting to the scope of the invention in any respect and should not be so construed.

EXAMPLE 1 PREPARATION OF THIELOCIN (1) Fermentation of *Thielavia terriola* RF-143

After cultivation of *Thielavia terriola* RF-143 on a potato-glucose agar slant at 28° C. over 7–10 days, the resultant whole cells and spores on the slant were used to inoculate a medium (800 ml) in a 2 L volume Erlenmeyer flask, said medium having the following composition: glucose 2.0 %; polypeptone 1.0 %; meat extract 0.3 %; yeast extract 0.2 %; and sodium chloride 0.1 % (pH 7.0). The inoculated flask was subjected to shaking culture at 28° C. for two days. The cultivated medium (800 ml) was added to fresh medium (20 L) having the same composition as above in a 30 L volume jar fermentator, and aerobic spinner cultivation was conducted at 28° C. for one day (aeration: 20 L/minute, stirring: 150 rpm). A 6 L portion of the resultant vegetative medium was transferred to a 250 L fermentation tank containing a medium (150 L) of the composition: potato exudate (200 g/L) and sugar (20 g/L), no pH adjustment. Fermentation was carried out at temperature of 28° C. with a stirring rate of 20 rpm over 16 hours, and then at 370 rpm over seven days. Aeration was conducted at 150 L/minute (1.0 vvm).

(2) Isolation

A. Crude Extraction

The fermentation broth obtained above (146 L) was adjusted to pH 3.0 by the addition of diluted HCl, and filtered. The filtrate was adjusted to pH 2.5, added with sodium chloride (7 kg), and extracted with ethyl acetate (36 L). On the other hand, the filter cake was extracted twice with 80 % acetone (18 L each), and the extracts were combined and concentrated to a volume of 7 L. After addition of water (6 L), the concentrate was extracted with ethyl acetate (18 L) at pH 2.5.

The ethyl acetate extracts obtained above were combined and concentrated to a volume of 15 L under vacuum. The concentrate was extracted three times with water adjusted to pH 8.1 by the use of diluted aqueous sodium bicarbonate. The extracts were combined and extracted with ethyl acetate (20 L) at pH 2.5. The ethyl acetate extract was washed with water (6 L) and concentrated to dryness under vacuum to obtain crude powder (82 g) containing thielocin.

B. Purification (1)

The crude powder (82 g) obtained above was dissolved in acetone (400 ml), adjusted to pH 8.0 with diluted aqueous sodium hydroxide, and added to water (1.2 L). Resultant precipitates were filtered, and the filtrate was applied to HP-20 column (Mitsubishi Chemical) (5 L). The column was developed with a gradient solvent comprising acetone - 20 mM phosphate buffer, pH 7.5, (1:9). Fractions containing activity were combined, and evaporated under vacuum to remove the acetone. To the residue was added water, and the aqueous solution was extracted with ethyl acetate at pH 2.0. The extract was washed with water, concentrated to dryness under vacuum, and washed with petroleum ether. Partly purified thielocin (29 g) was thus obtained.

C. Purification (2)

The partly purified thielocin (15 g) was dissolved in acetone (40 ml), and 20 mM phosphate buffer (130 ml) pH 7.5, was added thereto. The resultant solution was applied to CHP-20p column (5×42 cm) (Mitsubishi Chemical). The column was washed with acetone-20 mM phosphate buffer, pH 7.5, (1:9), and developed with a gradient solvent comprising the just-mentioned solvent and pure acetone. Fractions containing activity were eluted out at an acetone concentration of about 50-60 %. The fractions were collected and adjusted to pH 3.5 with the addition of diluted phosphoric acid to yield brown precipitates. The precipitates were filtered and dissolved in methanol (40 ml), and the methanol solution was applied to a silica gel (Merk) column (4.6×30 cm). The column was developed with a solvent of chloroform:methanol:water (62:25:4), and fractions (about 200 ml) containing activity were obtained. After concentration of the fractions to about 20 ml, the concentrate was purified by high pressure liquid chromatography using Nucleosil 5C$_{18}$ column (2.0×20 cm) (Machery-Nagel Co.) and acetonitrile:0.1 % phosphate (57:4). A fraction containing α-thielocin and a fraction containing β-thielocin are separately obtained and concentrated. Each concentrate was extracted with ethyl acetate, and the extract was washed with water, dried over anhydrous sodium sulfate, and concentrated to dryness. This gave 35 mg of α-thielocin as a colorless powder (mp: 190°-194° C.) and 20 mg of β-thielocin as a colorless powder (mp:244°-247° C.).

(3) Analysis

Thin layer chromatography failed to separate α-thielocin from β-thielocin. High pressure liquid chromatography conducted under conditions listed below provided different retention volumes of 17.6 ml and 28.4 ml for α-thielocin and β-thielocin respectively (see FIG. 1 (a) and (b)).

Column: Nucleosil 5C$_{18}$4.6ϕ×150 mm
Mobile phase: Acetonitrile:0.1 % phosphate (55:45)
Flow rate: 2.0 ml/min.
Chart speed: 0.5 cm/min.
Detection: Absorption at 220 nm The physico-chemical properties of α- and β-isomers so separated are listed below.

Thielocin α

Figure 2:
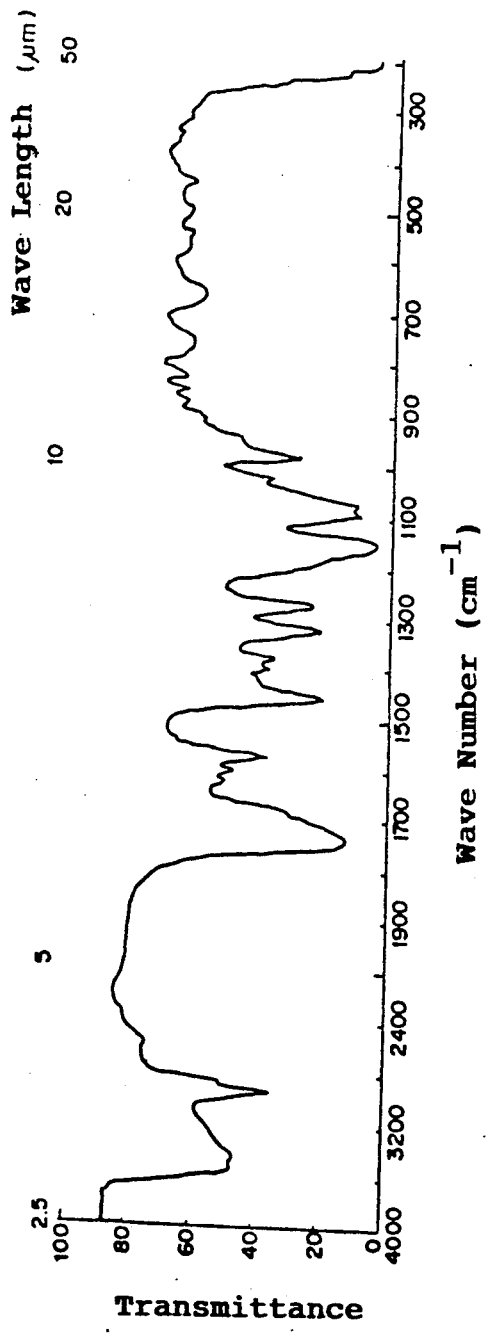
FIG. 2 shows IR spectra of α-thielocin (FIG. 2 (a)) and of β-thielocin (FIG. 2 (b)).
Figure 2:
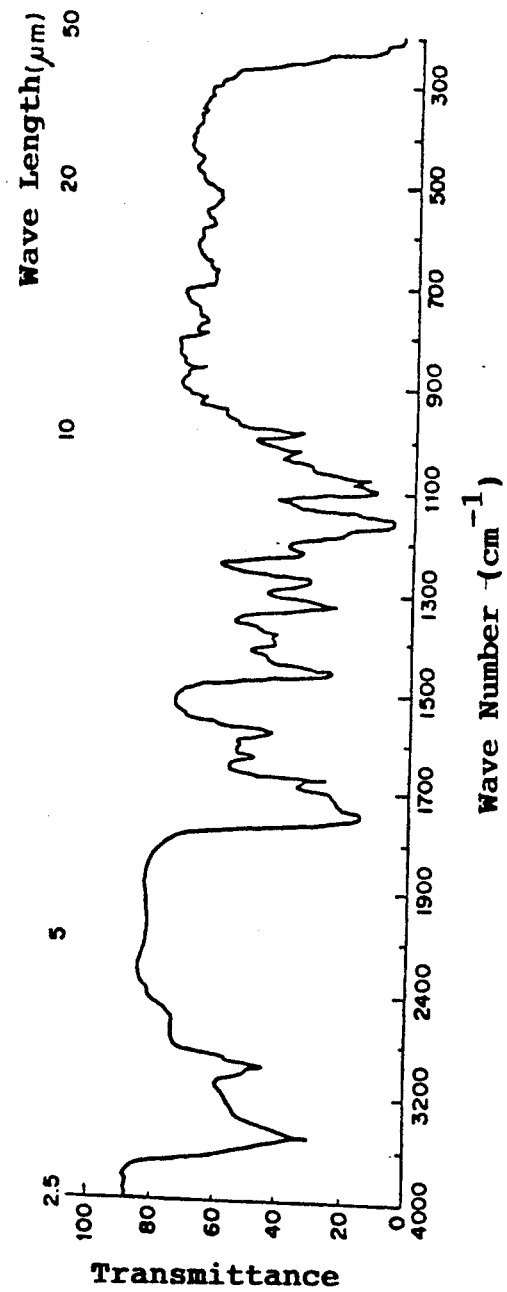

1. Empirical formula: $C_{54}H_{60}O_{18}$ (M.W. 996)
2. Elementary analysis (for $C_{54}H_{60}O_{18} \cdot H_2O$);
   Found: C, 63.52; H, 6.28;
   Calculated: C, 63.91; H, 6.11
3. SI-MS: m/z 997 (M+1)
4. Melting point: 190°-194° C.
5. Solubility: Soluble in dimethylsulfoxide, acetonitrile, chloroform, ethyl acetate, and acetone; slightly soluble in methanol and ethanol; sparingly soluble or insoluble in ethyl ether, hexane, petroleum ether, and water
6. IR spectrum (KBr): FIG. 2(a); shows absorption at the following frequencies (cm$^{-1}$): 3560-3440, 2950, 1740-1675, 1575, 1460, 1325, 1275, 1150, 1095, 1070, and 985.
7. UV spectrum (MeOH): end absorption, 245 nm (shoulder), 275 nm (shoulder)
8. CD (CHCl$_3$) almost zero at 230-300 nm
9. NMR spectrum: as shown in Table 1

| 10. Color reaction: | Ninhidrin | Negative |
|---|---|---|
| | FeCl$_3$ | Negative |
| | (under neutral or acidic condition) | |

11. Others: acidic and colorless powder

Thielocin β

1. Empirical formula: $C_{54}H_{60}O_{18}$ (M.W. 996)
2. Elementary analysis (for $C_{54}H_{60}O_{18} \cdot H_2O$);
   Found: C, 63.63; H, 6.06 ;
   Calculated: C, 63.91; H, 6.11 ;
3. SI-MS: m/z 997 (M+1)
4. Melting point: 244°-247° C.
5. Solubility: Soluble in dimethylsulfoxide, slightly soluble in acetonitrile, chloroform, ethyl acetate, acetone, methanol, and ethanol; sparingly soluble or insoluble in ethyl ether, hexane, petroleum ether, and water
6. IR spectrum (KBr): FIG. 2(b); shows absorption at the following frequencies (cm$^{-1}$): 3490, 2950, 1740-1675, 1577, 1460, 1325, 1272, 1222, 1155, 1095, 1075, 1050, and 985.
7. UV spectrum (MeOH): end absorption, 245 nm (shoulder), 275 nm (shoulder)
8. CD (c: 0.0782, CHCl$_3$): $[\theta]_{260}0$, $[\theta]_{267}-300, [\theta]_{270.5}-110, [\theta]_{277.5}-230, [\theta]_{285}0$
9. NMR spectrum: as shown in Table 1

| 10. Color reaction: | Ninhidrin | Negative |
|---|---|---|
| | FeCl$_3$ | Negative |
| | (under neutral or acidic condition) | |

11. Others: acidic and colorless powder

Table 1 below shows $^1$H and $^{13}$C NMR data for α-thielocin and β-thielocin, which have been determined at 24° C. using CDCl$_3$-CD$_3$OD (20:1) as a solvent and TMS as an internal standard.

TABLE 1

| α-Thielocin (about 45 mg/0.6 ml)<br>$^1$H NMR data<br>δ (multiplicity, proton number) | β-Thielocin (Saturated)<br>$^1$H NMR data<br>δ (multiplicity, proton number) |
|---|---|
| 1.519(s, 3H) | 1.330(s, 3H) |
| 1.752(s, 3H) | 1.890(s, 3H) |
| 2.134(s, 3H) | 2.233(s, 3H) |
| 2.192(s, 3H) | 2.238(s, 3H) |
| 2.209(s, 3H) | 2.264(s, 3H) |
| 2.217(s, 3H) | 2.269(s × 2, 6H) |
| 2.24(s × 2, 6H) | 2.274(s, 3H) |
| 2.248(s, 3H) | 2.295(s × 2, 6H) |
| 2.282(s × 2, 6H) | 2.322(s × 2, 6H) |
| 2.343(s, 3H) | 2.396(s, 3H) |
| 2.370(s, 3H) | 2.406(s, 3H) |
| 2.396(s, 3H) | 2.742(d(J = 16), 1H) |
| 2.720(d(J = 16), 1H) | 3.300(d(J = 16), 1H) |
| 3.380(d(J = 16), 1H) | 3.833(s × 3, 9H) |
| 3.775(s, 3H) | 3.348(s, 3H) |
| 3.809(s, 3H) | |
| 3.821(s × 2, 6H) | |
| $^{13}$C NMR data<br>δ(multiplicity, carbon number) | $^{13}$C NMR data<br>δ(multiplicity, carbon number) |
| 9.25(q, 1) | 9.14(q, 1) |
| 10.19(q × 2, 2) | 10.23(q × 2, 2) |
| 10.52(q, 1) | 10.58(q, 1) |
| 13.01(q × 2, 2) | 13.05(q × 2, 2) |
| 13.23(q, 1) | 13.29(q, 1) |
| 15.77(q, 1) | 15.82(q, 1) |
| 16.09(q, 1) | 16.43(q, 1) |
| 16.79(q × 2, 2) | 16.80(q × 2, 2) |
| 17.28(q, 1) | 17.33(q, 1) |
| 22.61(q, 1) | 22.33(q, 1) |
| 23.28(q, 1) | 22.67(q, 1) |
| 28.84(t, 1) | 30.11(t, 1) |
| 49.52(s, 1) | 46.73(s, 1) |
| 62.01(q × 2, 2) | 62.00(q × 3, 3) |
| 62.06(q × 2, 2) | 62.09(q, 1) |
| 76.16(s, 1) | 74.59(s, 1) |
| 100.05(s, 1) | 97.99(s, 1) |
| 116.82(s, 1) | 115.98(s, 1) |
| 116.91(s, 1) | 117.18(s, 1) |
| 121.37(s, 1) | 121.20(s, 1) |
| 121.80(s, 1) | 121.83(s × 2, 2) |
| 121.83(s, 1) | 122.29(s, 1) |
| 122.18(s, 1) | 125.55(s × 2, 2) |
| 125.53(s × 2, 2) | 126.01(s, 1) |
| 125.92(s, 1) | 126.27(s, 1) |
| 126.24(s, 1) | 127.85(s, 1) |
| 127.84(s, 1) | 127.93(s, 1) |
| 127.93(s, 1) | 129.54(s, 1) |
| 128.71(s, 1) | 132.15(s, 1) |
| 132.15(s, 1) | 133.22(s, 1) |
| 132.19(s, 1) | 133.33(s, 1) |
| 132.58(s, 1) | 133.45(s, 1) |
| 133.32(s, 1) | 148.89(s, 1) |
| 148.86(s, 1) | 149.07(s, 1) |
| 149.04(s, 1) | 149.37(s, 1) |
| 149.23(s, 1) | 150.45(s, 1) |
| 150.41(s, 1) | 152.92(s × 2, 2) |
| 152.91(s × 2, 2) | 154.06(s, 1) |
| 154.03(s, 1) | 154.80(s, 1) |
| 154.62(s, 1) | 158.73(s, 1) |
| 160.44(s, 1) | 163.99(s, 1) |
| 163.84(s, 1) | 166.35(s, 1) |
| 166.31(s, 1) | 166.75(s, 1) |
| 166.63(s, 1) | 170.42(s × 2, 2) |
| 170.50(s × 2, 2) | 196.30(s, 1) |
| 194.52(s, 1) | |

Note: s: singlet, d: doublet, t: triplet, q: quartet, J: spin coupling constant

The above NMR data shows that both α- and β-isomers contain 56 protons attributable to 18 methyl groups (including 4 methoxy groups) and one methylene group, when an interchangeable proton is excluded.

The above $^{13}$C NMR data also shows that both α- and β-isomers contain 18 methyl carbons, one methylene carbon, and 35 quarternary carbons, and hence, consist of 54 carbon atoms.

Experiment 1

PLA$_2$ inhibitory activities of thielocin were determined according to the following procedure.

Method

PLA$_2$ released from thrombin-stimulated rat platelets was prepared by immuno-affinity chromatography using antibody MD 7.1-coupled Sepharose (Murakami et. al, J. Biochem 104: 884–888, 1988). The standard assay conditions included, 250 μl of Tris-HCl buffer (100 mM, pH 7.4), CaCl$_2$ (3 mM), 40 μM [$^{14}$C] phosphatidylethanolamine and enzyme. The reaction was started by the addition of the enzyme solution. Following incubation at 37° C. for 20 min the reactions were terminated by addition of 1.25 ml of Dole's reagent (Dole, V. P. & H, Meinerts, J. Biol. Chem 235: 2595–2599, 1960). Then released free fatty acid was extracted, and counted in Liquiflour (Du Pont-New England Nuclear) to determine the release of the radioactivity. Inhibition activity is expressed as percent of enzyme control.

Test Results

Thielocin concentration required for exhibiting 50 % inhibitory activity was 47 μg/ml for porcine-derived PLA$_2$, 10 μg/ml for snake venom-derived PLA$_2$, 0.005 μg/ml for rat platelet-derived PLA$_2$. α-Thielocin and β-thielocin were equilibrated in the reaction solution, then the inhibitory concentrations were not distinguished each other.

What is claimed is:

1. A compound of the formula:

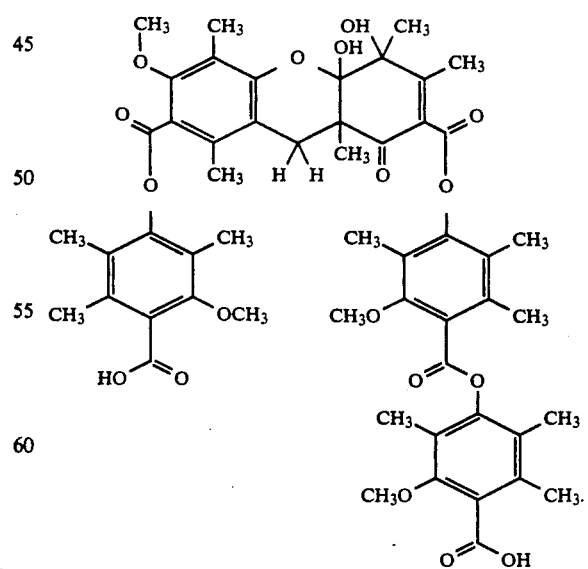

* * * * *